(12) United States Patent
Raghuprasad

(10) Patent No.: US 8,469,709 B2
(45) Date of Patent: Jun. 25, 2013

(54) DENTAL HYGIENE DEVICE

(76) Inventor: Puthalath Koroth Raghuprasad, Odessa, TX (US)

( * ) Notice: Subject to any disclaimer, the term of this patent is extended or adjusted under 35 U.S.C. 154(b) by 323 days.

(21) Appl. No.: 13/022,670

(22) Filed: Feb. 8, 2011

(65) Prior Publication Data

US 2012/0202172 A1 Aug. 9, 2012

(51) Int. Cl.
*A61C 17/00* (2006.01)
(52) U.S. Cl.
USPC ........................................................... 433/80
(58) Field of Classification Search
USPC .................... 433/5–7, 80; 128/859, 861–862, 128/848; 601/164; 600/237
See application file for complete search history.

(56) References Cited

U.S. PATENT DOCUMENTS

| | | |
|---|---|---|
| 4,064,628 A | 12/1977 | Weitzman |
| 5,323,787 A | 6/1994 | Pratt |
| 6,068,475 A | 5/2000 | Stoyka |
| 6,660,029 B2 | 12/2003 | VanSkiver et al. |
| 7,029,690 B1 | 4/2006 | Wehrli |
| 7,661,430 B2 | 2/2010 | Mason |
| 8,105,079 B2 * | 1/2012 | Farrell .............................. 433/6 |
| 2008/0280251 A1 | 11/2008 | Gallagher |
| 2009/0114228 A1 * | 5/2009 | Kirschner ................ 128/206.13 |

FOREIGN PATENT DOCUMENTS

| | | |
|---|---|---|
| GB | 2464492 | 4/2010 |
| JP | 3018357 | 1/1991 |
| JP | 2008088095 | 4/2008 |
| KR | 20040086889 | 10/2004 |

* cited by examiner

*Primary Examiner* — Sunil K Singh
(74) *Attorney, Agent, or Firm* — David L. King

(57) ABSTRACT

A dental hygiene device for wearing in the mouth over the teeth and along gums has a flexible open-support structure and a fabric covering overlying the support structure. The flexible open-support structure has two opposing facing bases, an inner base and an outer base. Each base extends the length of the device and has a curvature to fit over the teeth and along gums of a wearer of the device. The inner base fits between teeth and the tongue, while the outer base fits between the teeth and the cheeks and lips region of the mouth. A plurality of arch-shaped ribs extends from the inner base over to the outer base joining the two bases to form the flexible open-support structure. The fabric covering extends from each base overlying the plurality of arched ribs. The fabric covering is permeable to fluids. The support structure has a means for receiving and holding a cream or paste and delivering the cream or paste to the teeth, gums and fabric covering. The fabric covering is automatically wetted by the production of saliva allowing the cream or paste to wick and migrate into the fabric covering.

16 Claims, 11 Drawing Sheets

DENTAL HYGIENE DEVICE

TECHNICAL FIELD

This invention relates to a dental hygiene device that can be worn while sleeping, over the teeth and gums and provided with an antimicrobial or germicidal cream to keep the breath clean, treat or protect the teeth and gums while reducing the occurrence of morning breath.

BACKGROUND OF THE INVENTION

A common occurrence of bad breath is often experienced when one awakes from sleeping. The source of this bad breath is bacteria and other germs that grow and form in the mouth overnight.

In the morning, the person will brush his or her teeth and often use a disinfecting mouthwash. Most people find that a good brushing or flossing of the teeth right before going to bed further helps reduce this problem.

For others, the occurrence of morning breath happens regardless of the efforts to reduce it before one goes to sleep. For those people a more proactive measure to reduce germs build up in the mouth is needed.

For most people, good dental hygiene before going to bed and upon waking up reduces the problem, but does not eliminate it. For the majority of people a device that works overnight, fighting germ build up in the mouth would be very beneficial.

A secondary issue is that when traveling it is often inconvenient to brush or floss one's teeth. This is particularly true in long air flights. In these circumstances the travelling passenger has little opportunity to brush his teeth or use a mouthwash. In these cases, travelers often rely on chewing gum or breath mints to mask the problem. Ideally a solution is needed that doesn't just cover up the odor, but in fact eliminates the source of the odor, the germs in the mouth.

One objective of the present invention is to provide a device suitable for wearing comfortably while sleeping.

Another objective of the invention is to provide a way in which an antibacterial paste or cream can be slowly distributed in the area of the teeth, gums and mouth to fight germ build-up over as much as eight to ten hours.

These and other objectives are achieved by the device of the present invention as described as follows.

SUMMARY OF THE INVENTION

A dental hygiene device for wearing in the mouth over the teeth and along gums has a flexible open-support structure and a fabric covering overlying the support structure. The flexible open-support structure has two opposing bases, an inner base and an outer base. Each base extends the length of the device and has a curvature to fit over the teeth and along gums of a wearer of the device. The inner base fits between teeth and the tongue, while the outer base fits between the teeth and the cheeks and lips region of the mouth. A plurality of arch-shaped ribs extend from the inner base over to the outer base joining the two bases to form the flexible open-support structure. The fabric covering extends from each base overlaying the plurality of arched ribs. The fabric covering is permeable to fluids. The support structure has a means for receiving and holding a cream or paste and delivering the cream or paste to the teeth, gums and fabric covering. The fabric covering is wetted by the production of saliva allowing the cream or paste to wick and migrate into the fabric covering. The flexible open structure, preferably, has a connecting spine longitudinally extending through each arched rib connecting each rib along the length of the support structure. The fabric covering overlies the arched ribs and the spine. The means for holding the cream or paste is an open channel extending along the entire length of the support structure. Each inner base and outer base has a recessed groove extending along the length of the support structure. In combination, these two recessed grooves form the open channel for receiving the cream or paste. Each inner base and each outer base has a plurality of holes extending from the recessed grooves outward toward the fabric covering overlying the support structure. These holes provide fluid passageways for the cream or paste to wick into the fabric covering when in use. Each inner base and outer base has an external flange extending outward from the base. The external flange has pocket for receiving and securing the fabric cover. Each external flange extends along the entire length of the support structure. The fabric covering has an arch-shaped cross section to fit onto the support structure and into the flange pockets. The fabric covering preferably is formed or molded into the arch shape. The fabric covering has a pair of enlarged edges which are formed or molded longitudinally extending along the length of the fabric covering. The enlarged edges fit into the flange pockets to secure the fabric covering in the support structure. Preferably, the flange includes a projection extending outwardly to help secure and hold the fabric covering against the base. The fabric covering is removable and washable. Accordingly, after use the fabric covering can be removed from the support structure and thoroughly cleaned. The support structure is made of a durable flexible plastic or elastomeric material, preferably soft enough to not irritate the teeth or gums and yet with enough rigidity to provide a spring-like clamping action to hold the device securely onto the teeth and gums while wearing. The fabric covering is, preferably, made of a porous or synthetic open cell foam material or a natural fabric which are water insoluble, but water permeable. The arched ribs are shaped to form a flexible spring-like closure wherein the opposing forces of the inner base and outer base are in contact and whereupon when inserting the device over the teeth and along the gums, they open keeping the inner base and outer base in good contact with the teeth and gums. The fabric covering upon being automatically wetted by saliva collapses onto the teeth along the open portions of the support structure under the movement of the tongue and cheeks of the wearer. The saliva acts to help liquefy the cream or paste and if the cream or paste is provided with an antimicrobial or antibacterial component, the cream or paste is then transferred throughout the mouth helping to keep the breeding of germs to a minimum and thereby helping to reduce the occurrence of bad breath. The cream or paste can be provided with an antibiotic or other medicant for treating the gums and/or teeth, or a whitening agent for the teeth and can also be treated with a fresh smelling scent to provide a freshness of the breath and a clean smelling breath.

The advantage of the present system is that it can be worn overnight providing six or eight hours or more of contact along the teeth, gums and mouth to provide an opportunity to provide medicants to the teeth and gum area and to provide an antibacterial capability over an extended period of time. It is anticipated that after a period of daily use, the device may be worn less often.

BRIEF DESCRIPTION OF THE DRAWINGS

The invention will be described by way of example and with reference to the accompanying drawings in which.

DETAILED DESCRIPTION OF THE INVENTION

Figure 3A:
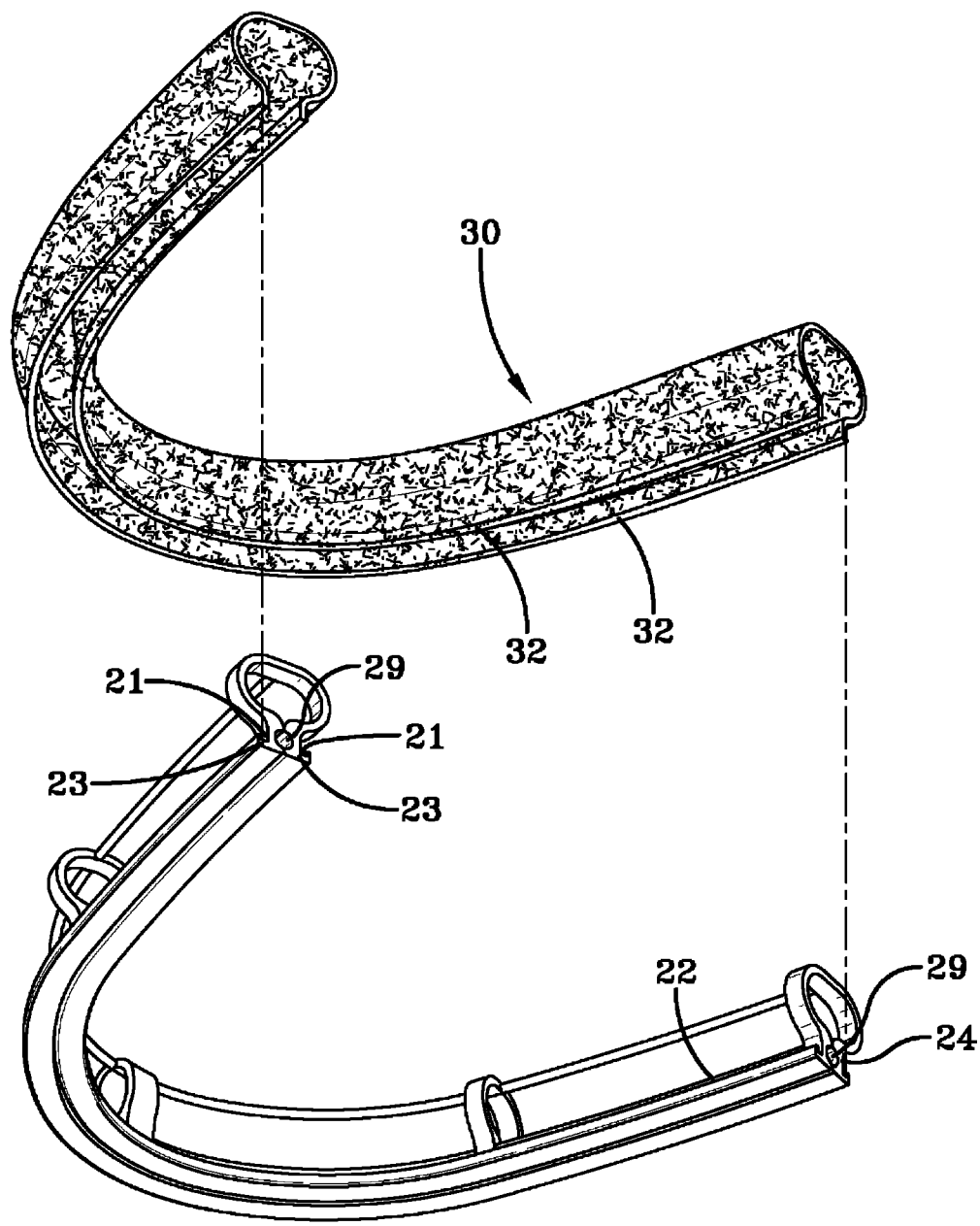
FIG. 3A is a first exploded view looking upwardly at the open support structure and the fabric covering prior to assembly.
Figure 3B:
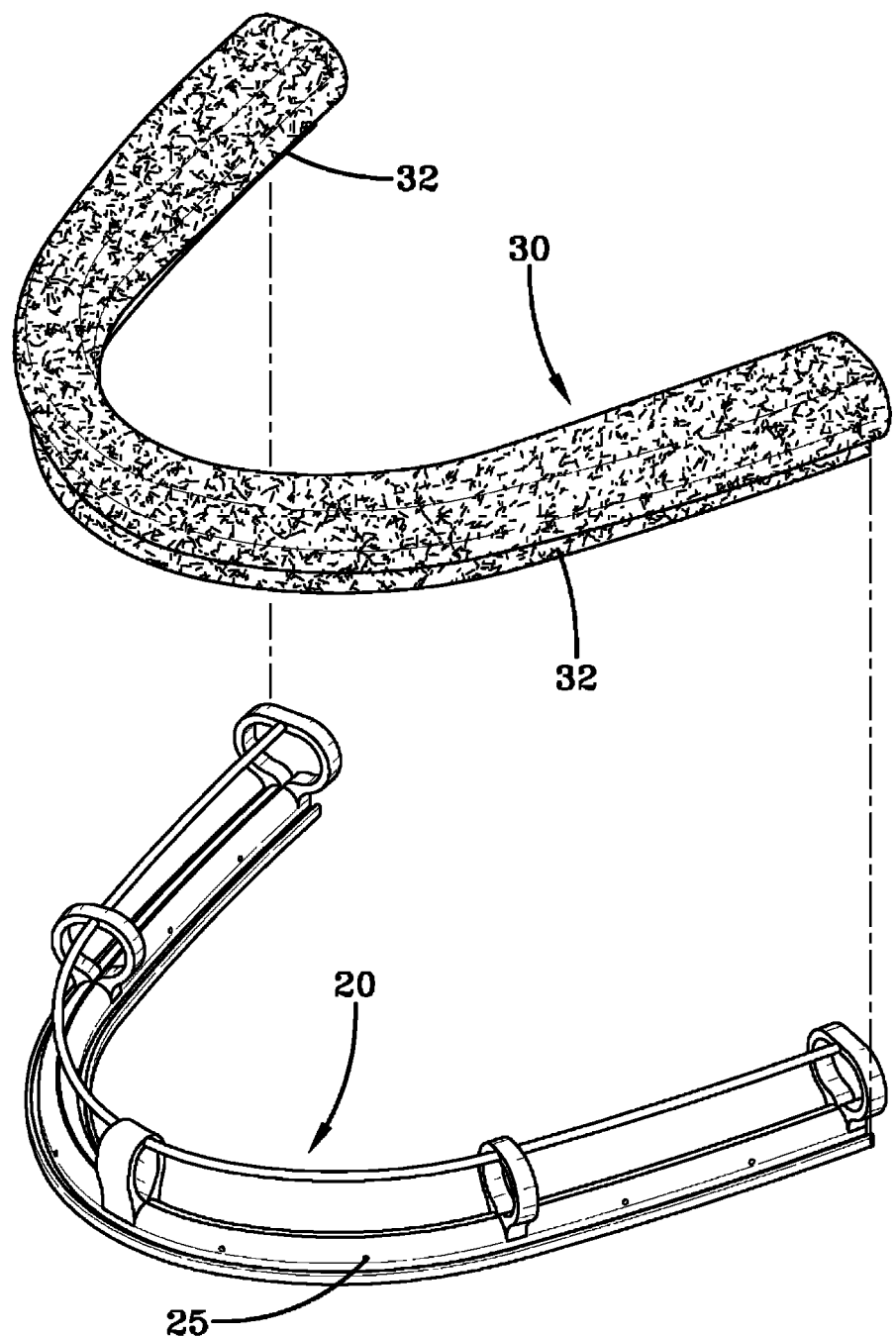
FIG. 3B is a second exploded perspective view looking downwardly at the fabric covering and open support structure prior to assembly.
Figure 4:
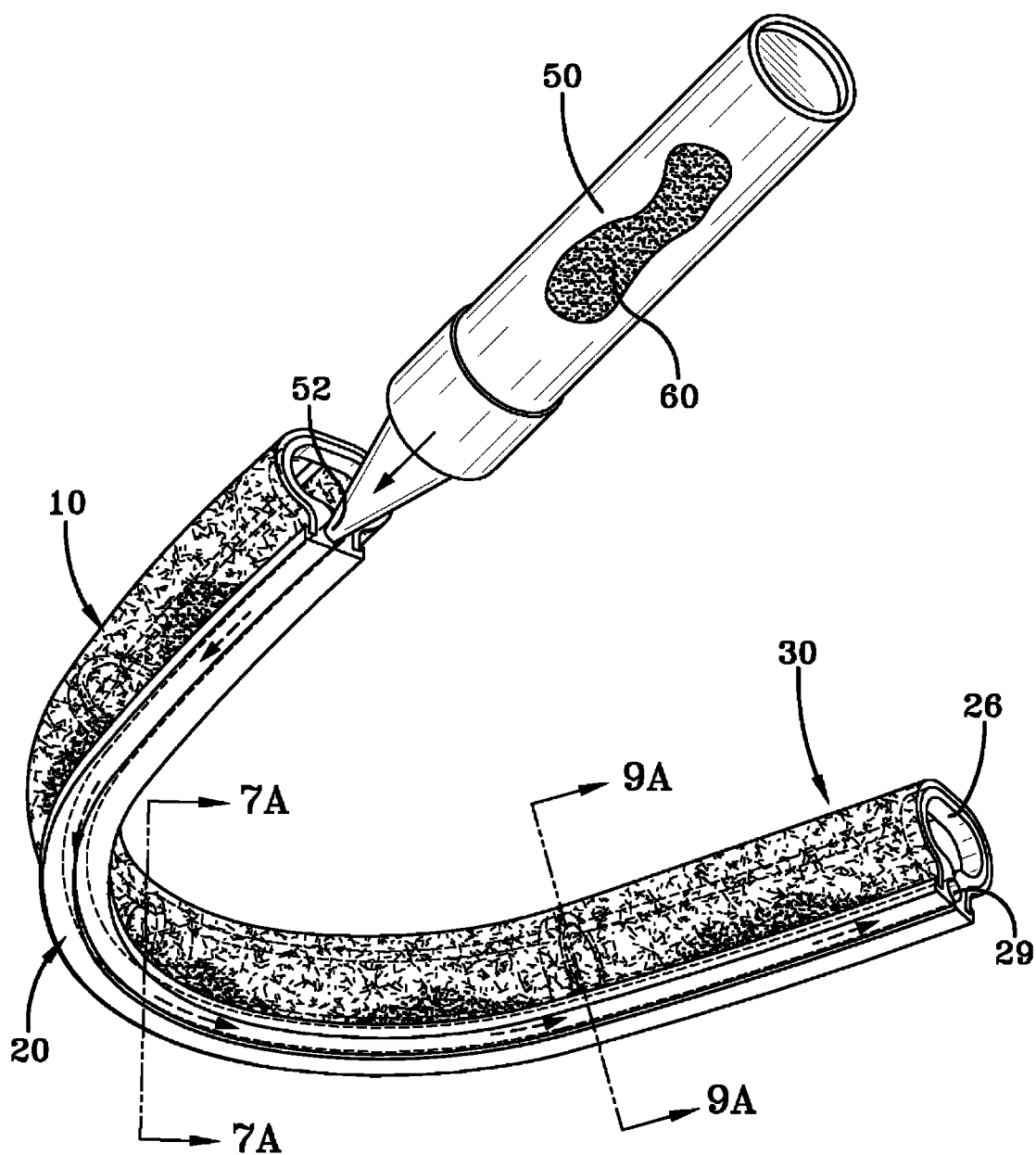
FIG. 4 is an upward looking perspective view of the dental hygiene device being filled with a cream or paste from a tube with a nozzle showing a preferred way of preparing the device according to the present invention.

With reference to FIGS. 1A-4, the dental hygiene device 10 of the present invention is illustrated. As shown in FIG. 4, the device 10 has an outer fabric covering 30 that overlays a flexible open-support structure 20. As shown in FIG. 4, a cream or paste can be applied into an open channel 29 of the device 10. This cream or paste moves in the direction of the arrow filling the channel 29 as illustrated.

Figure 1A:
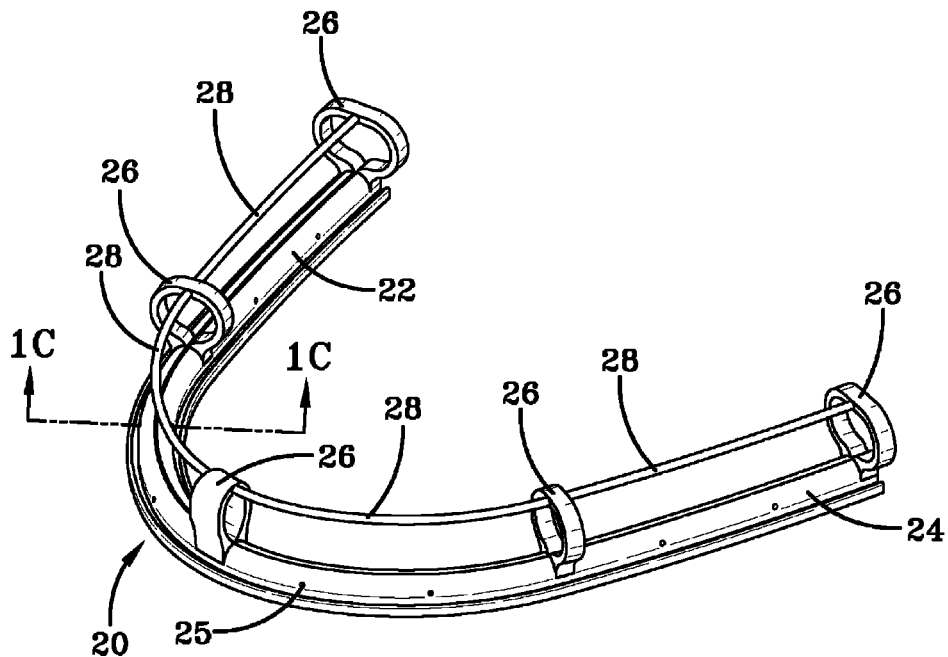
FIG. 1A is a first perspective view of the flexible open-support structure of the dental hygiene device of the present invention.
Figure 1C:
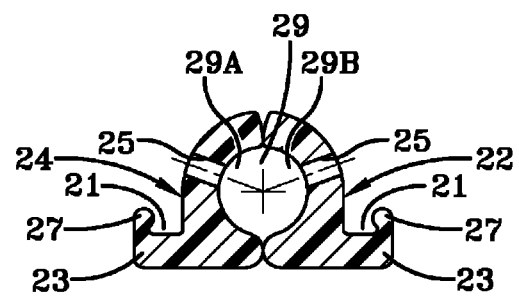
FIG. 1C is a cross sectional view of the support structure showing the two opposing inner and outer bases taken along section lines 1C-1C from FIG. 1A.
Figure 1B:
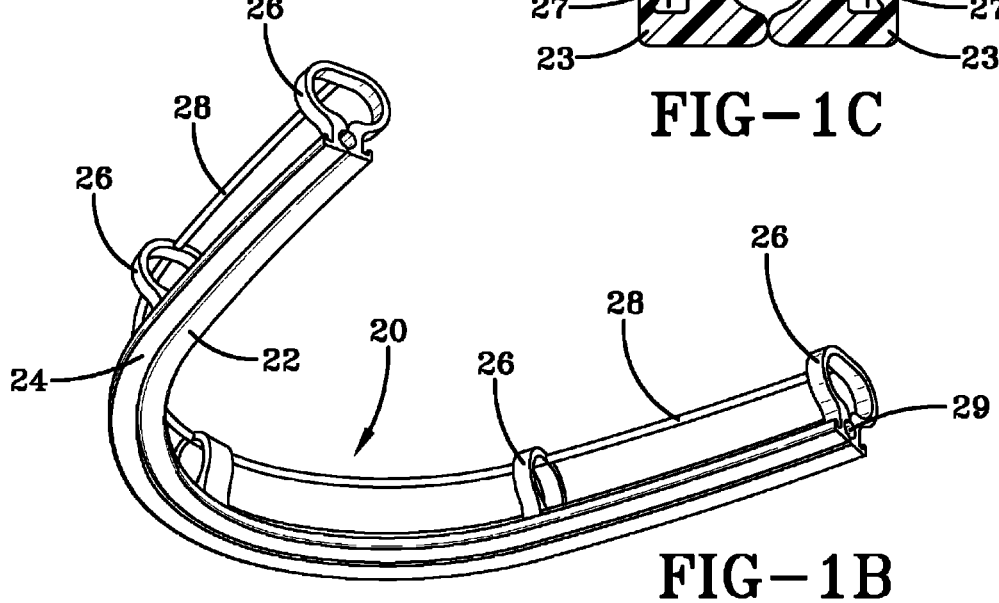
FIG. 1B is a second perspective view of the flexible open-support structure of FIG. 1A only looking upwardly from below the inner and outer base.

With reference to FIGS. 1A, 1B and 1C, the flexible open-support structure 20 is shown in greater detail. The flexible open-support structure 20 as shown has a pair of opposing bases 22 and 24; these opposing bases 22, 24 follow a curvature ideally suited to fit over a set of teeth either upper or lower. Connected to each base 22, 24 is a pair of arch-shaped ribs 26. The ribs 26 extend outward from the base in an arch shape and connect to the other base providing a secure spring-like connection between the two opposing bases 22 and 24. At the top surface of each arched rib 26 extends a longitudinally extending spine 28. The optional spine 28 extends along the length of the device connecting each arched rib 26. Large open spaces exist between the arched ribs 26, the spine 28 and bases 22, 24. As shown, inside each base 22, 24 are a plurality of holes 25 as illustrated in FIG. 1A and in greater detail in FIG. 1C. These holes 25 extend from an open channel 29. The open channel 29 is composed of two parts, a groove 29A and a groove 29B such that when the two opposing faced bases 22, 24 are in contact, the grooves form a complete channel 29 as illustrated. Holes 25 are openings that extend outward from the channel 29 into a region where a fabric covering 30 will be placed. As shown, at the bottom of each base 22, 24 is an outward extending flange 23 which extends upward to a projection 27. The projection 27 along with the inner base 22 or the outer base 24 forms a pocket 21 on each side of the respective base. This pocket 21 provides a way to secure a fabric covering 30 which will be installed later.

As shown in FIG. 1B from the bottom of the base, one can easily appreciate that the device 10 is held in a spring-like fashion wherein the channel 29 is maintained closed until the bases 22, 24 are separated apart.

Figure 2A:
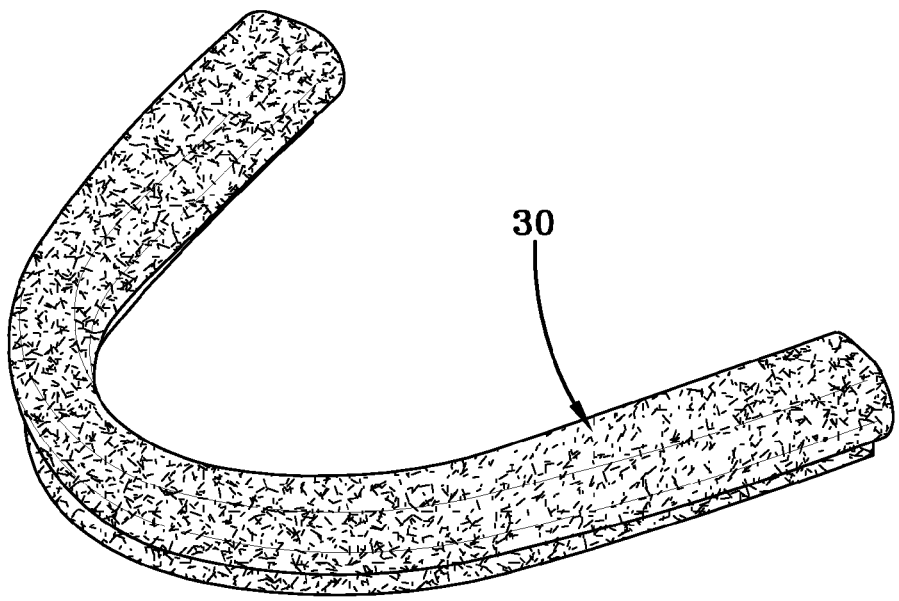
FIG. 2A is first perspective view of the fabric covering of the dental hygiene device of the present invention.
Figure 2B:
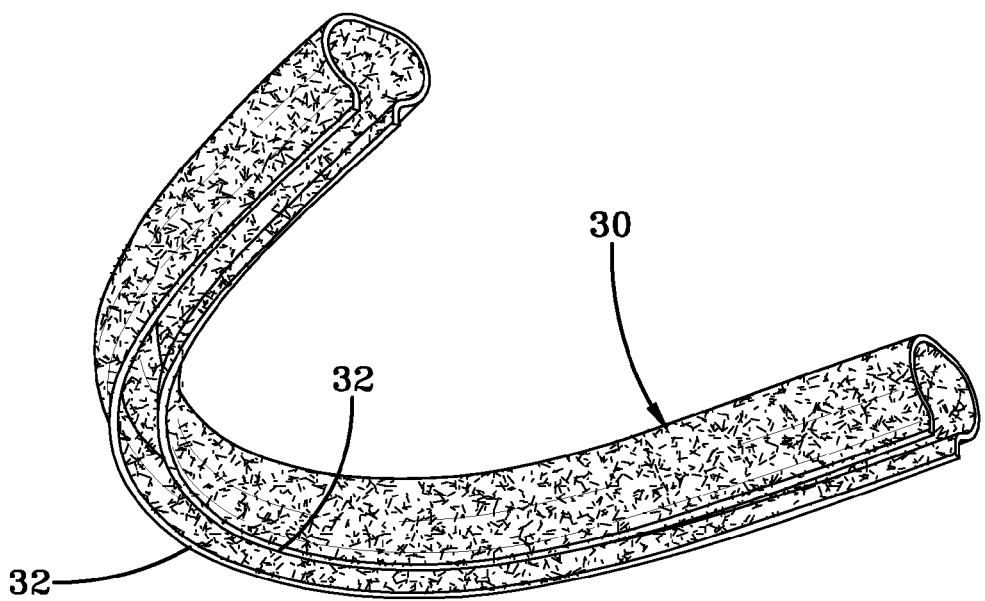
FIG. 2B is a second perspective view of the fabric covering of FIG. 2A, but looking upwardly from below the edges.

With reference to FIGS. 2A and 2B, the fabric covering 30 is disclosed. The fabric covering 30, as shown, follows the curvature similar to the open support structure 20 and longitudinally extends in such a fashion that it will fit over the open support structure 20. The fabric covering 30 has longitudinal edges 32 as illustrated, extending along each side of the woven fabric covering 30. As shown, the fabric covering 30 is preferably made of a fabric of textile or a synthetic open cell foam material that is water permeable and yet insoluble such that the fabric covering 30 as molded or formed has the arch like shape adapted to fit directly over the support structure 20.

With reference to FIGS. 3A and 3B, the fabric covering 30 is shown above the open support structure 20, illustrating how it is mounted into the support structure 20. The edges 32 fit directly into the pockets 21 at each side of the bases 22, 24. When assembled, the dental hygiene device 10 appears as shown in FIG. 4, at this point in time, the device 10 needs to be charged with a cream or paste. To do this, preferably a container 50 is provided with the paste or cream 60 inside the container 50 this container can be a tube or other flexible device with preferably a nozzle 52. The nozzle 52 is adapted to fit into the channel 29 formed between the two bases 22, 24. Upon squeezing the tube or container 50, the cream or paste 60 is pushed inwardly into the channel 29 and moves along the direction as illustrated. To fill the device, one simply squeezes the paste or cream 60 until it can be seen coming out the opposite end of the channel 29 of the device 10, at this point the device 10 is completely filled. If so desired, one can place an obstruction over the opposite end of the device 10 to ensure not only that the channel 29 fills, but the holes 25 can be filled with some of the cream or paste 60 extruding outwardly into the fabric covering 30. This filling the holes 25 with cream or paste 60 is not necessary as will be seen later when discussing how the device 10 is worn and used.

Figure 5:
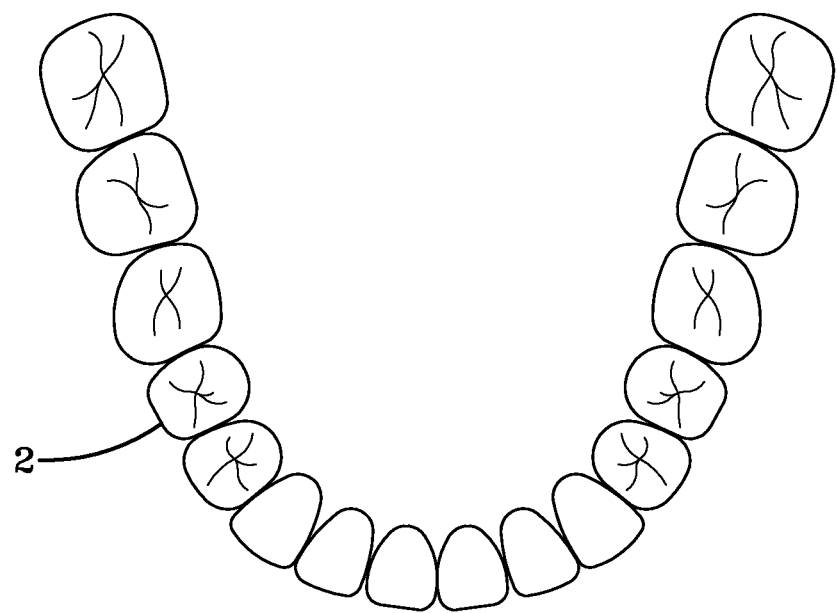
FIG. 5 is a plan view of a set of teeth.

With reference to FIG. 5, a plurality of teeth 2 are arranged as one would normally see in the lower part of the mouth.

Figure 6:
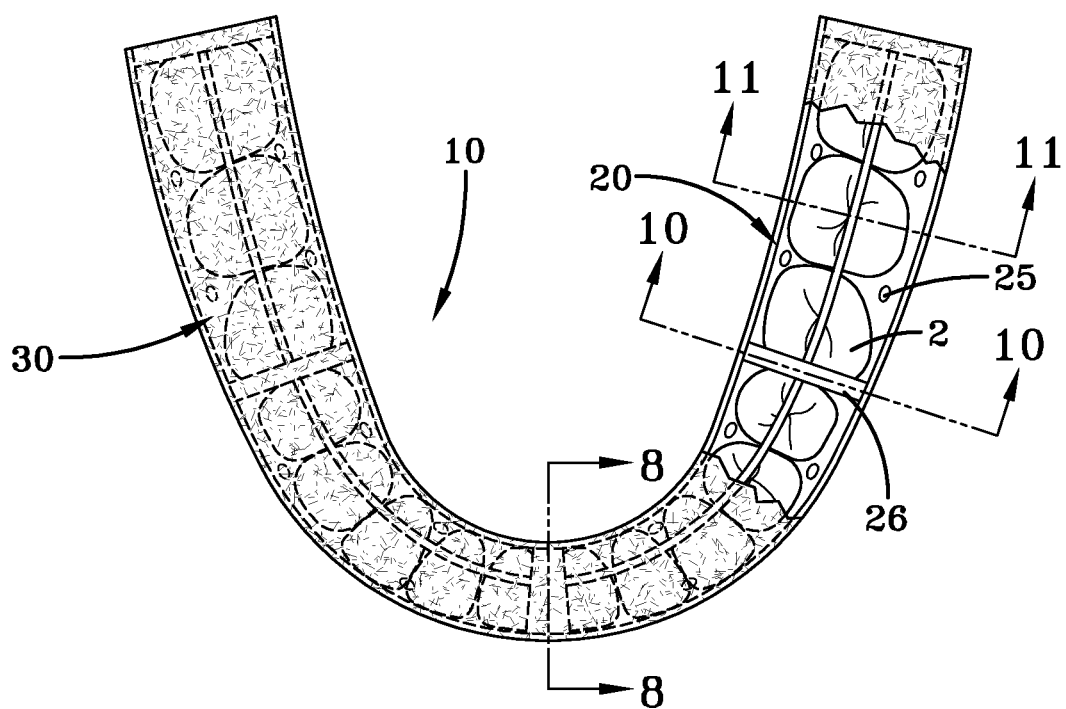
FIG. 6 is a plan view of the dental hygiene device mounted over the teeth.

With reference to FIG. 6, the device 10 is then inserted, once filled with cream or paste 60, over the teeth 2 as illustrated.

Figure 7A:
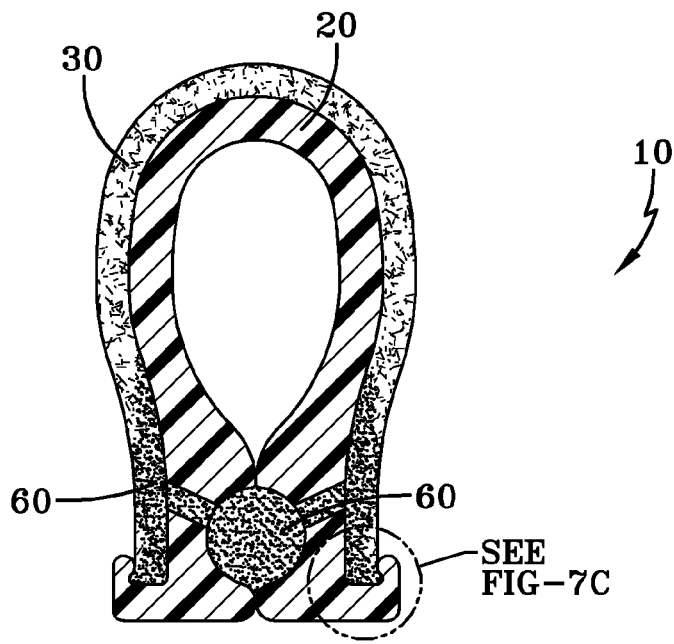
FIG. 7A is a cross sectional view of the dental hygiene device taken along lines 7A-7A of FIG. 4.

Prior to inserting the device 10 onto the teeth 2, after the channel 29 is filled with cream or paste 60 as shown in FIG. 7A, it can be seen that the fabric covering 30 starts to wick some of the fluid through the holes 25 up into the lower portion of the fabric covering 30. As shown in FIG. 7B, when the bases 22, 24 are spread apart under the spring-like action of the arched ribs, the paste or cream 60 separates into both sides of the device 10 providing an open surface longitudinally along the length of the device 10 wherein the cream or paste 60 is positioned to be in direct contact with teeth 2 along the gums 4 when fitted over the teeth 2 as shown in FIG. 5.

Figure 7C:
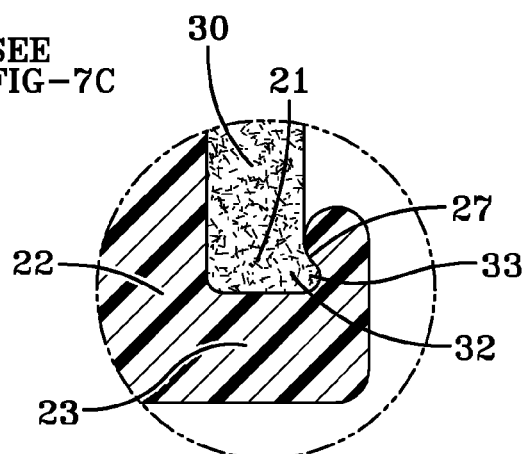
FIG. 7C is an enlarged view taken from FIG. 7A showing how the enlarged edge of the fabric covering fits into the flange pocket, securing the covering to the support structure.
Figure 7B:
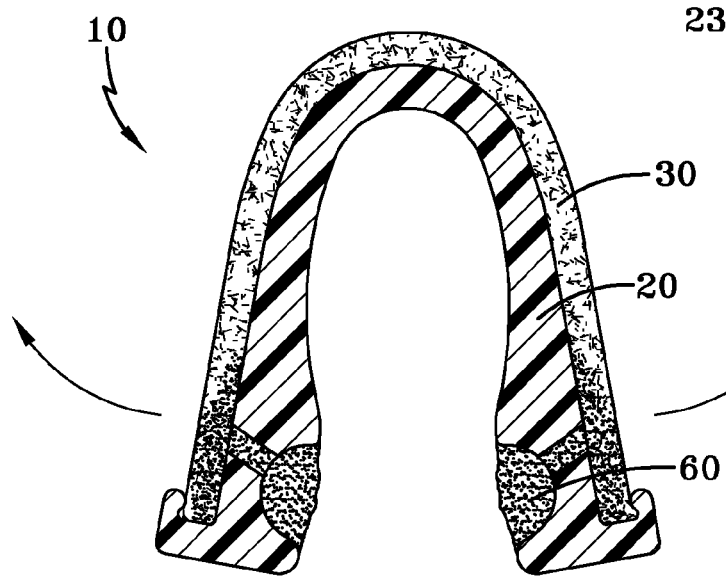
FIG. 7B is a cross sectional view of the device similar to FIG. 7A, but with the inner base and outer base pulled apart showing how the dental cream or paste adheres to both sides of the support structure.

With reference to FIG. 7C, the fabric covering 30 is shown having the edge 32 slightly enlarged by a fabric projection 33, the fabric projection 33 fits under the projection 27 and into the pocket 21 formed between projection 27 and the base 22 as shown. On the opposite side, the base 24 has a similar projection 27 and a pocket 21 allowing the edge 32 with its fabric projection 33 to snap in and be secured tightly into the open-support structure 20.

Figure 8:
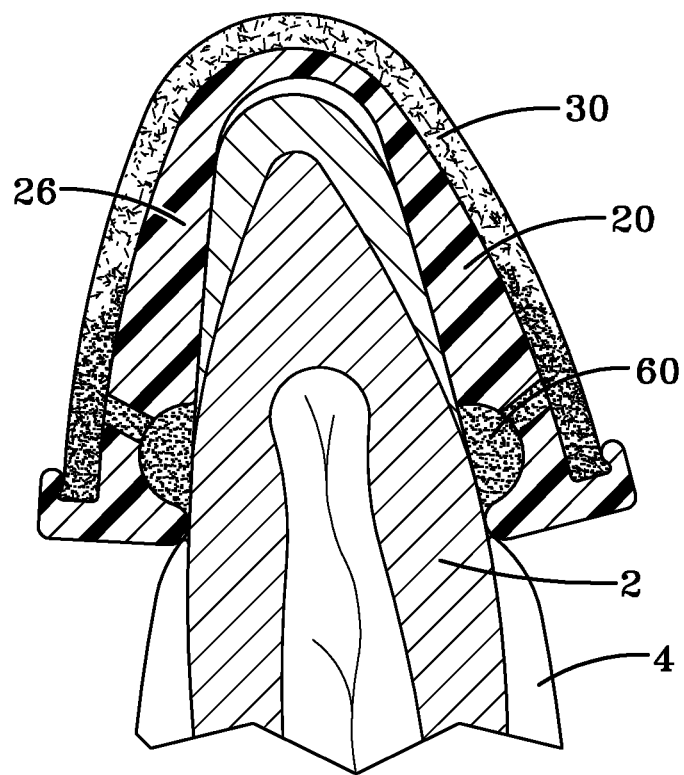
FIG. 8 is a cross sectional view of the dental hygiene device as it appears when mounted over the teeth.
Figure 9A:
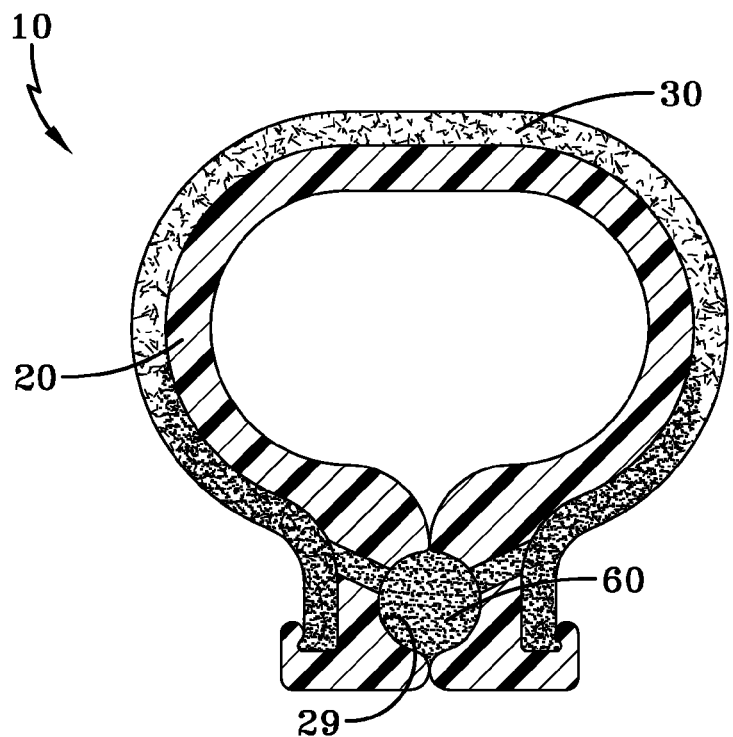
FIG. 9A is another cross sectional view taken along lines 9A-9A of FIG. 4 showing the device has a somewhat more open cavity for fitting on the molars.
Figure 9B:
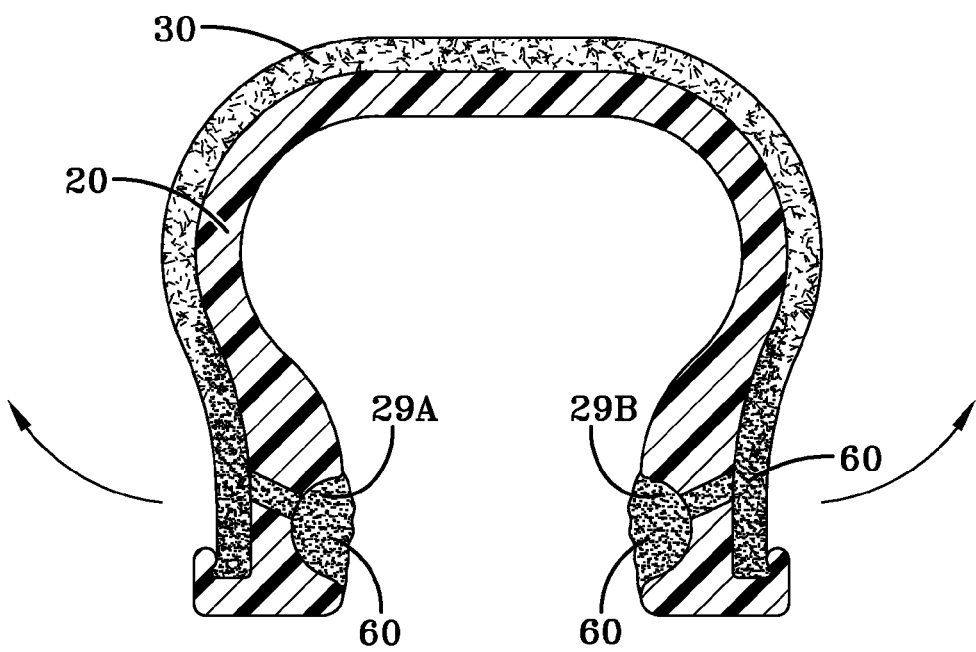
FIG. 9B is a cross sectional view showing the device's appearance when open to wear over the teeth
Figure 10:
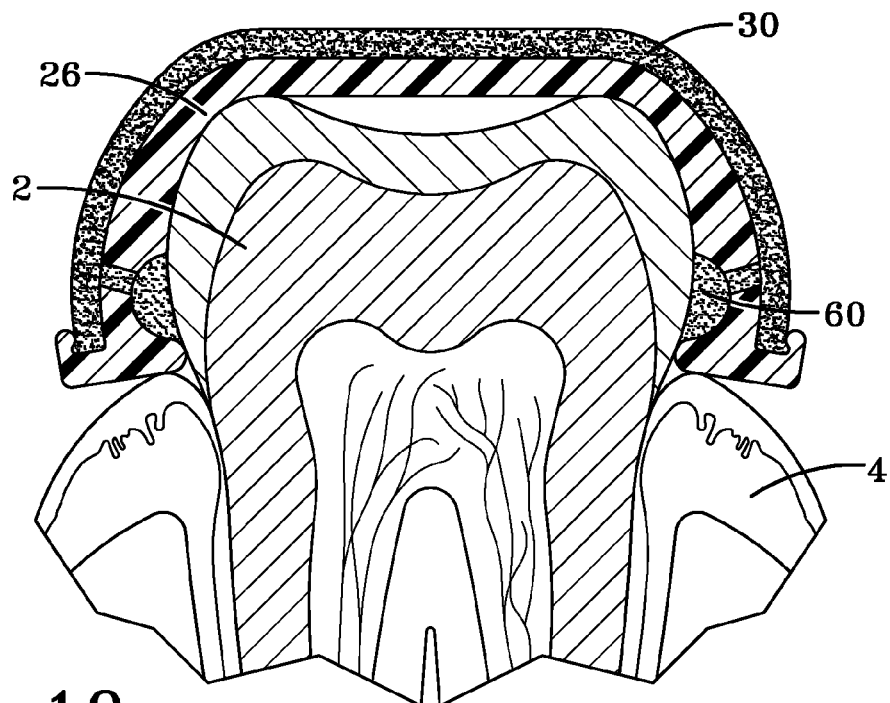
FIG. 10 is a cross sectional view showing the device mounted over a large molar tooth in the region of an arch rib.
Figure 11:
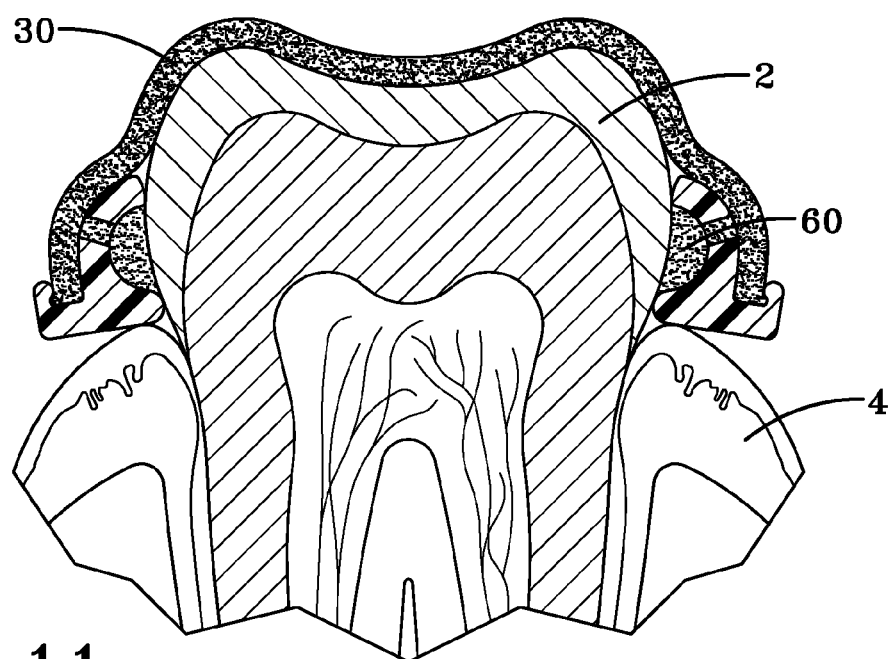
FIG. 11 is the same view as FIG. 10 in an open region between the arch ribs showing how the saliva laden fabric covering contacts the teeth.

In the cross sectional views of FIGS. 8, 9A, 9B, 10 and 11, the device 10 is shown after being charged with a cream or paste 60. In FIG. 8, the front portion of the device 10 is illustrated fitting over the front teeth 2 which are substantially narrower. The teeth 2 and the device 10 extend down to the gums 4 providing a fit over the teeth 2 and along the gums 4 in this area. With reference to FIG. 10, showing the rear portion of the device 10 when the bases 22, 24 are spread apart in such a fashion that the device 10 can fit over the shallower molars 2 which are substantially wider, therefore creating a more open appearance of the dental hygiene device 10. Again the device 10 fits directly over the teeth 2 and along the gums 4 as illustrated. The fabric covering 30 is shown in FIGS. 8 and 10 directly overlying one of the arched ribs 26. In FIG. 11, the fabric covering 30 is shown in the open space between the arched ribs 26. In this case, the optional spline 28 is not used or shown allowing the fabric covering 30 after being automatically wetted by the saliva to deform and lie directly onto the teeth 2 as illustrated. If there is sufficient compliance at the top surface of the device 10, the fabric covering 30 will droop or lay onto the optional spine 28, if used, above the teeth 2, but will be in direct contact along the side surfaces of the teeth 2. In this case, the paste or cream 60 can wick up into the fabric covering 30 and onto the teeth 2 and downward to the gums 4 as the saliva reduces the viscosity of the cream or paste 60 allowing it to migrate along the gums 4 and into the teeth 2 area. As illustrated, this device 10 is designed to be worn while a person sleeps. It can be worn over a period of several hours due to the pliant nature of the both the open support structure 20 and the fabric covering 30. The device 10 is adapted to be minimally invasive and of such light weight that the wearer can wear it comfortably without hampering his or her ability to sleep. As shown, the device 10 is mounted only on the lower set of teeth 2. However, it is designed such that the user may alternatively apply it to an upper set of teeth if so desired or can wear two devices, one on both an upper and lower set of teeth without any particular interference. It is believed preferable to only need one device 10 during an overnight's sleep in that it is the least intrusive for the user and would provide a complete solution to the morning breath problem commonly occurring for many people. As shown, the device 10 provides an excellent means for providing prolonged treatment with antimicrobial or other medicines for the teeth 2 and gums 4. This is of particular value in that most medicaments cannot currently be provided or applied over a period of time; due to the movement of the tongue over the treated area it is impossible to keep the medicines in contact with the treated area over any extended period of time. The present invention provides an ideal means for providing the medicants over an extended period of time, particularly at the edge line between the teeth 2 and the gums 4. This is particularly important in that the tongue can no longer wipe off the fluids or medicants trying to be provided to this region; as such it makes it possible for the wearer to get an extended treatment heretofore unavailable. This feature is particularly useful when treating conditions of dental or gum disease such as gingivitis. Antibiotics and steroids and other medicines can be used with this device 10 which can make the treatment shorter in overall duration and more effective, possibly eliminating the need to administer the antibiotics systemically by way of pills taken orally or injections. The present invention, as designed, has the fabric covering 30 made with a fabric material which is molded to the shape of the open support structure 30. This fabric covering 30 is removable and washable and therefore the entire device 10 can be cleaned and reused if so needed.

Figure 12:
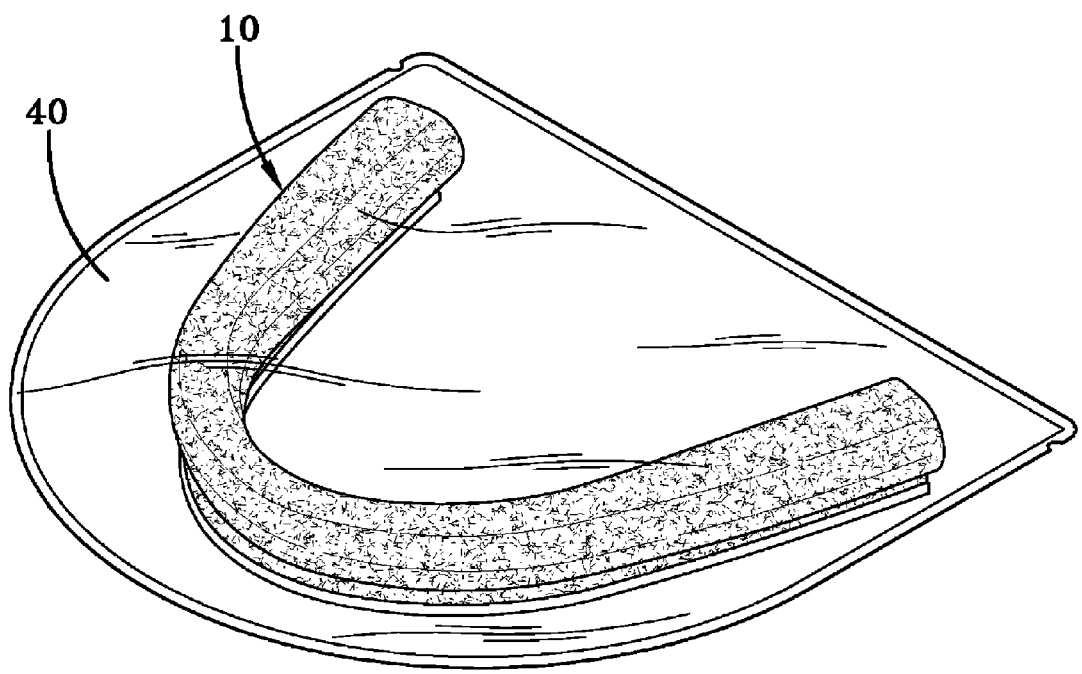
FIG. 12 is one embodiment of the dental hygiene device wherein the device is packaged and pre-loaded with dental cream or paste for convenient use; this embodiment is a preferred packaging of the device when used in air travel.

In FIG. 12 an alternative device 10 is shown that is virtually identical, however, in this device it is recommended that the dental hygiene device 10 be prefilled with the cream or paste 60 and that it be packaged either in a vacuum form or other air impermeable foil packaging so that the user may open the container 40 exposing the device 10 and placing the device 10 directly into the mouth such that it can provide a quick and easy means to provide some dental cleaning or whitening while the user is sleeping. It has been determined that in extended flights travelling overseas or in flights of more than 5 hours, the typical passenger likes to sleep. During this time, the traveller does not have a convenient opportunity to brush or floss the teeth. This device 10 provides a means to provide some dental hygiene while a person is travelling.

As can be easily appreciated, the dental hygiene device 10 as illustrated in the figures is ideally suited for creating a means for also whitening teeth. It has been determined that the bleaching and/or whitening requires a significant number of treatments in order to achieve any particular level of whitening. This device 10 is particularly useful in overcoming tea stains and other coffee stains from occurring causing the teeth to yellow. With the use of this device 10 with an appropriate whitener in the paste or cream 60, the device can be maintained in the mouth over a period of 6 to 8 hours or longer. This can provide an ideal way to provide a low concentration whitener that will enable the teeth to be treated as one sleeps to overcome the stains created during the day. Accordingly, this device 10 provides not only a means of reducing morning breath, it provides a means of treating the gums and teeth that may or may not have a particular disease or infection or alternatively can be used to achieve teeth whitening. These and other uses of the device 10 are contemplated within the scope of this invention. Alternatively, some variations in the design of the device 10 such as in the number of arches or the way in which the bases are connected in a spring-like fashion can alternatively be configured. However, it is believed important that a separate fabric covering 30 be provided to allow a wicking action to occur between the teeth 2 and the paste or fluid and that this separate fabric covering 30 be mounted onto an open structure to allow the paste or fluid to move freely within the mouth. This device 10 is particularly unique in that typical mouth guards that fit over the teeth and gum are solid plastic non-permeable devices that do not allow for the flow of the paste or cream 60 to be transferred easily into the mouth region. This is because mouth guards are solid plastic components usually made of a flexible material to protect the teeth 2 from impact. Alternatively, devices that provide for fluoride treatments used in the prior art are similarly solid containers in that the teeth are then pressed into a sponge like material encapsulated by a non-permeable support structure wherein the teeth and the medicament are contained entirely inside a non-permeable support structure.

These devices inherently are very inconvenient for the wearer and provide no easy means of applying in such a fashion that one could sleep with them in their mouths. As such they have been designed for use in dental offices for short duration treatments of a few minutes or less. The present device as described above allows for extended periods of wearing the device and that further allows for a way in which the device can be cleaned and reused if so desired. Alternatively, due to the low cost nature of the device it is deemed reasonable that these devices of the present invention could be prepackaged and used in a disposable fashion as illustrated in FIG. 12.

The Fabric covering 30 may include activated charcoal incorporated in the fabric material to remove existing odor in the mouth of the wearer.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A dental hygiene device for wearing in the mouth over the teeth and along the gums comprises;
    a flexible open-support structure, the flexible open-support structure having two opposing facing bases, an inner base and an outer base, each base extends the length of the device and has a curvature to fit over the teeth and along the gums of a wearer of the device, the inner base fits between the teeth and the tongue while the outer base fits between the teeth and cheek and lips region of the mouth, a plurality of arch-shaped ribs extend from the inner base to the outer base joining the two bases to form the flexible open-support structure;
    a fabric covering extends from each base overlying the plurality of ribs, the fabric covering being permeable to fluids; and
    wherein the support structure has a means for receiving and holding a cream or paste and delivering the cream or paste to the teeth, gums and to the fabric covering, wherein the fabric covering is wetted by the production of saliva allowing the cream or paste to wick and migrate into the fabric covering.

2. The dental hygiene device for wearing in the mouth over the teeth and along the gums of claim 1 wherein the flexible open-support structure has a connecting spine longitudinally extending between each arch rib connecting each rib along the length of the support structure; and wherein the flexible covering overlies the arch ribs and spine.

3. The dental hygiene device for wearing in the mouth over the teeth and along the gums of claim 1 wherein the means for holding the cream or paste is a channel extending along the length of the support structure.

4. The dental hygiene device for wearing in the mouth over the teeth and along the gums of claim 3 wherein each inner and outer base has a recessed groove extending along the length of the support structure, the combination of the two recessed grooves forms the channel.

5. The dental hygiene device for wearing in the mouth over the teeth and along the gums of claim 4 wherein each inner base and outer base has a plurality of holes extending from the recess groove outward toward the fabric covering overlaying the support structure.

6. The dental hygiene device for wearing in the mouth over the teeth and along the gums of claim 1 wherein each inner and outer base has an external flange extending from each base, the external flange has a pocket for receiving and securing the fabric covering, each external flange extends along the length of the support structure.

7. The dental hygiene device for wearing in the mouth over the teeth and along the gums of claim 6 wherein the fabric covering has an arch-shaped cross section to fit onto the support structure and into the flange pocket.

8. The dental hygiene device for wearing in the mouth over the teeth and along the gums of claim 6 wherein the fabric covering has a formed or molded arch shape.

9. The dental hygiene device for wearing in the mouth over the teeth and along the gums of claim 8 wherein the fabric covering has an enlarged edge formed or molded along the length, the enlarged edge fits into the flange pocket to secure the fabric covering in the support structure.

10. The dental hygiene device for wearing in the mouth over the teeth and along the gums of claim 9 wherein the fabric covering is removable.

11. The dental hygiene device for wearing in the mouth over the teeth and along the gums of claim 9 wherein the fabric covering is washable.

12. The dental hygiene device for wearing in the mouth over the teeth and along the gums of claim 1 wherein the support structure is made of a flexible plastic or elastomer.

13. The dental hygiene device for wearing in the mouth over the teeth and along the gums of claim 1 wherein the fabric covering is made of a porous synthetic open cell foam or natural fabric which is water insoluble, but water permeable.

14. The dental hygiene device for wearing in the mouth over the teeth and along the gums of claim 1 wherein the arch ribs are shaped to form a flexible spring-like closure of the inner base and opposing outer base, wherein upon inserting over the teeth open keeping the inner base and outer base in contact with the teeth and along the gums.

15. The dental hygiene device for wearing in the mouth over the teeth and along the gums of claim 1 wherein the fabric covering upon being wetted by saliva collapses onto the teeth in the open portion of the support structure under the movement of the tongue and cheeks of the wearer.

16. The dental hygiene device for wearing in the mouth over the teeth and along the gums of claim 1 wherein the fabric covering has activated charcoal incorporated in the fabric material.

* * * * *